Figure 1:
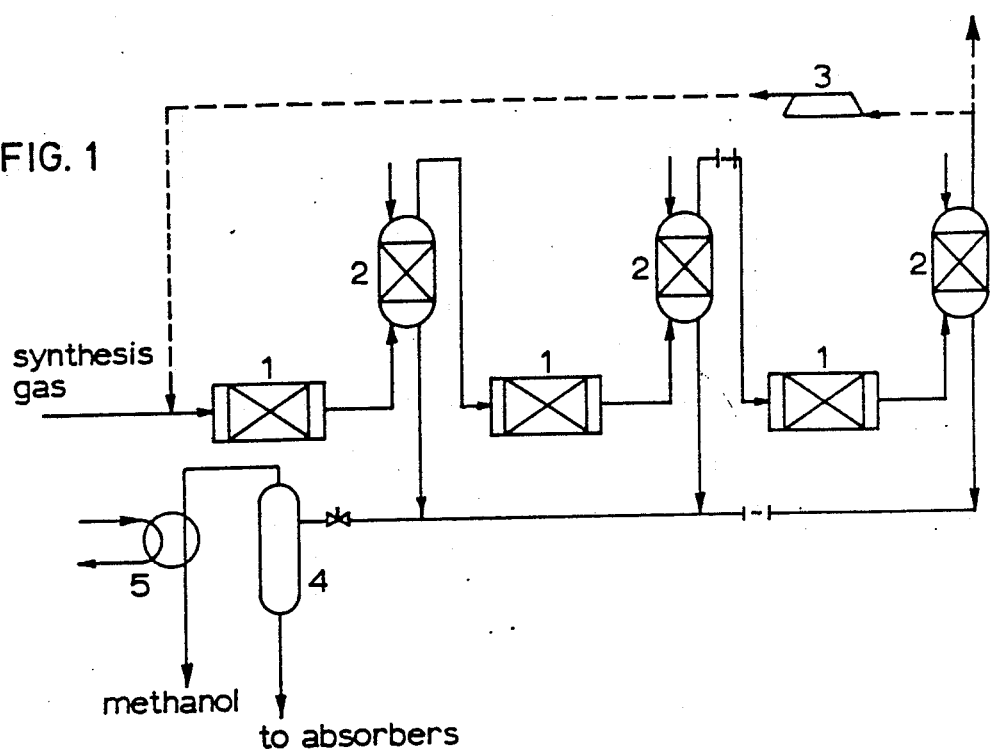

United States Patent [19]

Westerterp

[11] Patent Number: 4,968,722

[45] Date of Patent: Nov. 6, 1990

[54] PROCESS FOR PRODUCING METHANOL

[75] Inventor: Klaas R. Westerterp, Mozartlaan, Netherlands

[73] Assignee: Process Engineering Consultants PEC B.V., Enschede, Netherlands

[21] Appl. No.: 305,806

[22] Filed: Feb. 1, 1989

[30] Foreign Application Priority Data

Feb. 5, 1988 [EP] European Pat. Off. ........ 88200207.4

[51] Int. Cl.$^5$ ...................... C07C 27/06; C07C 29/15; C07C 29/76
[52] U.S. Cl. .................................. 518/706; 518/713; 518/724; 518/725
[58] Field of Search ................ 518/706, 724, 725, 713

[56] References Cited

U.S. PATENT DOCUMENTS 2,497,932  2/1950  Dart ..................................... 518/724
3,950,369  4/1976  Gent ............................. 518/713 U X
4,529,738  7/1985  Sugier et al. ......................... 518/713
4,595,701  6/1986  Nakamura et al. .................. 518/700

FOREIGN PATENT DOCUMENTS 1259945  1/1972  United Kingdom ................ 518/706

Primary Examiner—Howard T. Mars
Attorney, Agent, or Firm—Zarley McKee, Thomte, Voorhees & Sease

[57] ABSTRACT

A process for producing methanol by reacting carbon monoxide and hydrogen, wherein said reactants in the gaseous phase are introduced into a reaction zone comprising one or more fixed catalyst beds using a liquid absorbent, selectively absorbing substantially all of the methanol formed, followed by desorption of the methanol. The absorption of methanol is preferably effected in a separate absorption zone.

9 Claims, 2 Drawing Sheets

PROCESS FOR PRODUCING METHANOL

This invention relates to a process for producing methanol by reacting carbon monoxide and hydrogen and optionally carbon dioxide, wherein said reactants in the gaseous phase are introduced into a reaction zone comprising one or more fixed catalyst beds using an absorbent, selectively absorbing substantially all of the methanol formed, followed by desorption of the methanol.

At present, methanol production is almost exclusively based on a direct hydrogenation of carbon-monoxide according to the following equation:

and if the reactants contain carbon dioxide, also:

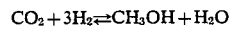

To obtain reasonable reaction rates, (solid) catalysts have to be used. An important progress has been noticed in this field in the last 15 years: highly active copper catalysts replaced the old zinc-based catalysts, allowing a reduction of the process pressure from 20–30 MPa to 5–10 MPa and of the temperature by about 50 K, down to 485–550 K.

Methanol synthesis is a strongly exothermic ($\Delta H_{298} = -91$ KJ/mol) equilibrium reaction. An increase in the temperature infavourably influences the position of the reaction equilibrium. Moreover, the copper catalysts loose their activity very quickly if their maximum allowable operating temperature has been exceeded due to an insufficient heat removal. As a consequence the reaction never can go to completion in the reactor, in passing through the catalyst bed the reaction slows down and even stops at approaching the equilibrium composition at reactor conditions of pressure and temperature.

Two types of reactors are presently used for the methanol synthesis: adiabatic bed reactors and cooled tubular reactors. An adiabatic bed reactor consists of several fixed catalyst beds in series. The temperature in the sections is controlled either with heat exchangers between the beds or by introducing cold synthesis gas between the catalyst beds. In this "cold shot" construction no heat exchangers are needed in the reactor. The main disadvantage is, however, the dilution of the product by the "cold-shot" gas, increasing the costs of the product separation from the reactor effluent.

A cooled tubular reactor e.g. consists of a bundle of tubes filled with the catalyst. The tubes are installed in a cooling jacket and cooled e.g. by boiling water so that steam is generated. This construction makes the reactor temperature easy to control.

Due to the infavourable position of the reaction equilibrium at process temperature, the methanol concentration in the non-condensable reactor effluent is low: the methanol molar fraction usually does not exceed a value of 0.1. Therefore, the separation of the reaction product by condensation causes essential difficulties and the heat transfer coefficients are very low so that large heat exchange areas in the condenser are required.

Because of the incomplete conversion, the unconverted reactants have to be recycled to the reactor inlet by means of a compressor. The recycle ratios are commonly in the range of 5 to 10 for methanol plants.

When looking for possibilities to lower the methanol production costs, in the first place methods to increase the singlepass conversion and to decrease the reactant recycle ratios or even to suppress the recycling completely should be taken into consideration.

To this end the so-called Gas-Solid-Solid Trickle Flow (GSSTF) reactor has been developed. In this reactor the product is removed from the reaction zone by means of a countercurrent stream of solid particles of a selective methanol adsorbent which keeps the methanol concentration in the gas phase very low, so that the driving force for the forward reactions remains high. A technical-economical evaluation of the GSSTF-system for the synthesis of methanol showed great savings a.o. in circulation energy, cooling water consumption and also the amount of catalyst required. As reported in European patent application No. 218,285 the high pressure GSSTF-reactor has been proved to be completely successful on miniplant scale.

The GSSTF system has the disadvantage that the solid adsorbent has to be recycled, which is not a common technique.

Now it is found, that this problem can be avoided by replacing the solid adsorbent by a selective liquid absorbent: pumping and flashing of liquid streams are easy, well-mastered operations, much better than the solids handling in a GSSTF reactor.

However, in a gas-liquid-solid system, inevitably the reaction will be hampered by additional mass transfer resistances over the liquid film at the catalyst surface and especially inside the pores. This will result in an ineffective utilization of the catalyst activity and, accordingly, in an excessive reactor volume.

According to another aspect of the invention a process for producing methanol is provided wherein in the reaction zone only the reaction of carbon monoxide and hydrogen and optionally carbon dioxide occurs, the effluent from the reaction zone being fed to an absorption zone where methanol is absorbed.

It is preferred that the unreacted reactants after the absorption step are fed to one or more subsequent systems comprising a reaction zone and an absorption zone as defined above. Such a system comprising reaction zones and absorption zones is shown in FIG. 1. In absorbers 2 after each reactor 1 a selective removal of methanol from the gaseous reaction mixture takes place, thus increasing again the driving force for the (equilibrium) reaction by taking away the product after passing each reactor.

Each reactor contains a fixed bed of the catalyst on which surface the reaction takes place. The reactors can be either of the adiabatic or of the cooled tubular type. The gaseous effluent of a reactor passes through an absorber, where the reaction product is removed from the gas stream by selective absorption in a solvent. The gas stream leaving the absorber now has a low methanol content and is fed for further conversion to the subsequent reactor.

After passing each absorber the volume of the reaction mixture is reduced because of the removal of methanol from the gas stream. Therefore each subsequent reactor or absorber will be smaller than the previous one. This will lead to an important saving in the total reactor volume required for the same methanol production in comparison with today's processes using the reactant recycle loop. Further in FIG. 1 as well as in FIG. 2 discussed below a recycle compressor 3, an expansion and a methanol condensor 5 are shown.

Figure 2:
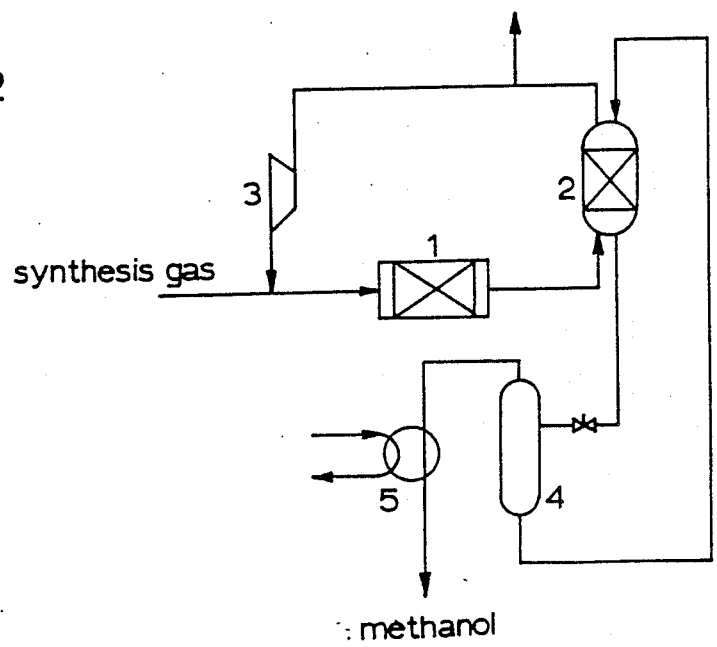

It is also possible to apply a system comprised only of a single reactor-absorber system in which the methanol-free synthesis gas is recycled from the absorber outlet back to the reactor inlet, see FIG. 2. In this way a high product yield can be achieved too. In this case, the per-pass conversion of reactants is similar to that of conventional methanol systems. The advantage of our system with a single reactor-absorber system lies in the fact that in that case the large and expensive heat exchange and condensing equipment in the recycle loop is replaced by a simple and inexpensive absorption desorption circuit for the methanol solvent, whereas the reactor and the absorber operate at the same temperature level.

For a system consisting of two or more reactor-absorber units not only savings in this recovery section, but also a significant reduction of the recycle of reactants is achieved, so that a much smaller recycle compressor is required and if 4 or more reactorsabsorbers sets are installed in series, we can even abstain from a recycle of non-converted reactants because only a very small amount of the unconverted synthesis gas will leave the last absorber. Carbon efficiencies of higher than 90% can easily be obtained in a system with four reactor-absorber sets. The small stream of off-gases can e.g. be used as fuel gas. The flow rate of inerts will remain constant all along the entire reactor train, provided they are not co-absorbed in the methanol absorbent. This means that the concentration level of inerts increases in the downstream direction, so that the reaction is retarded due to the dilution of the reactants. Therefore, relative to the feed rate somewhat more catalyst has to be installed in the downstream reactors.

Any conventional contact apparatus, e.g. packed column or plate column, is suitable as a methanol absorber.

The recovery of methanol from the saturated solvent can be achieved by any of the usual methods, in particular by:
(1) flashing of the liquid to a lower pressure,
(2) heating-up of the liquid up to a temperature level at which methanol desorbs completely or
(3) a combination of these two methods.

Usually, it cannot be avoided that some amount of synthesis gas, although small, will be co-absorbed in the solvent. In order to improve the yield on raw materials, these minor amounts of synthesis gas can be recirculated to the reactors for a further conversion. In order to minimize the energy demand for this recirculation it is desirable to desorb the synthesis gas at a high pressure level. This can be achieved in two-stage flashing train. In the first stage, operating at a relatively high pressure, a predominant portion of synthesis gas is released and recirculated to the reactors. In this stage no or only a small portion of methanol desorbs. The second expansion stage is operated at a relatively low pressure allowing a complete release of methanol.

The reactors are operated at a temperature level which allows a high activity of the catalyst used. For the modern copper catalysts the desirable temperature range is 210° to 280° C. The process pressure also depends on the properties of the catalyst used and usually lies in the range of 4 to 10 MPa.

The absorption of methanol takes place outside the reaction zones and therefore in principle it can be carried out at any temperature. Generally, at lower temperatures a higher methanol solubility can be expected. However, in order to achieve an optimum energetic efficiency of the system, it is preferred to operate the absorber(s) at a temperature level not too far removed from the operation temperature(s) of the reactor(s) and preferably at the same temperature of the reactor inlet as required to activate the reaction.

If the converters used are of the cooled tubular type, the entire heat of reaction released at the catalyst surface is removed through the reactor walls and utilized e.g. in steam production. In the case of the adiabatic reactor operation an interstage cooling of the reaction mixture is necessary to maintain the catalyst beds below the allowable temperature limit. Commonly this is achieved by interstage cooling or interstage injections of cold synthesis gas in-between the reaction sections. In the reactor-absorber system the interstage cooling can also be accomplished in the absorbers, so that the solvent also plays the role of the cooling medium.

The most important requirements with respect to the liquid absorbent are:
(1) good solubility of methanol,
(2) good selectivity for methanol,
(3) low saturated vapour pressure at reactor inlet conditions, and
(4) good thermal stability at operating conditions.

Any solvents satisfying these requirements will be suitable. Exemplary absorbents include tetra ethylene glycoldimethyl ether (TEGDME), sulfolane, 18-crown-6, etc. TEGDME is preferred.

To illustrate experimentally the principle of the invention a high-pressure miniplant has been built in which a reactor, an absorber and a reactor were lined-up in series. The miniplant was also provided with a solvent loop with a desorber unit and recirculation system. The unit can be operated continuously.

The high pressure miniplant (FIG. 3) consisted of two identical packed tubular reactors, each with an inner diameter of $25*10^{-3}$ m and a length of 0.5 m. Each reactor contained 360 grams of the BASF S3-85 copper catalyst, consisting of cylindrical pellets of $5 \times 5$ mm. Each reactor was equipped with an electrical heater and two thermocouples: one installed axially in the catalyst bed and the other at the outer side of the reactor tube wall. The thermocouples installed inside the catalyst bed were used to measure the reaction temperature, whereas the thermocouples at the reactor walls were coupled to Eurotherm type 810 electronic temperature regulators. A small diameter absorber is installed: we decided to use a packed bed column in view of its simplicity and flexibility. In model experiments a proper geometry for the column enabling a stable countercurrent operation, no flooding, good wetting of the packing and a good radial distribution of the liquid, was determined in a series of tests with a glass apparatus at ambient conditions. Various column diameters and packing materials have been examined. We chose a column diameter of $11*10^{-3}$ m and a packing material consisting of glass spheres with a diameter of $3.1*10^{-3}$ m. The height of the packed bed was 0.4 m. The absorber temperature was measured with a thermocouple installed axially in the packed bed, with its weld positioned $30*10^{-3}$ m above the lower end of the packing. The diameter of this thermocouple was 0.5 mm. Calculations showed that for an almost complete absorption of the methanol in TEGDME the column should have been about 1.0 m high.

Carbon monoxide was drawn from a battery of high pressure storage cylinders, while the hydrogen was supplied from the high pressure gas network of our high pressure laboratory. After passing Tescom type 2600 pressure regulators 1, pressure gauges 2 and the Brooks type 5850 TR electronic mass flow controllers 3 both gas streams were mixed in a helical mixing pipe 4. The synthesis gas was then preheated in an electrical preheater 6 and introduced into the first reactor 7. The methanol rich reactor effluent then entered into the absorber column 8 at the bottom. The gas leaving the column passed through a demister 9 and then entered into the second reactor 10. The process pressure was adjusted with a Tescom type 26-1700 hand-loaded back pressure controller 12 installed downstream of the second reactor. A 100 ml cold trap vessel 11 was installed just before the pressure controller in order to prevent the condensation of methanol in the downstream piping. The rate of condensation was determined by weighing the condensate accumulated during a well determined period of time. The flow rate of the dry effluent was measured with a wet gas meter 13. Also in all the other parts of the high-pressure section of the miniplant by installing electrical heating elements special care was taken to prevent methanol condensation.

The absorbent liquid was circulated by means of an Orlita membrane pump 21. Prior to entering the absorber the methanol-free liquid was preheated to the desired absorption temperature. Both the absorber and the liquid preheater 22 were equipped with heating jackets coupled with a Tamson type TC45/250 thermostatic bath 23. Mobitherm type 603 oil of Mobil was used as the heat transfer medium. Methanol and possibly co-absorbed carbon monoxide and hydrogen were liberated by flashing to a lower pressure. Either a single-stage or a two-stage flashing was possible by bypassing one of the flash vessels 20. Between the absorber 8 and the first flash vessel 20 a buffer vessel 15 with a liquid level indicator 16, and electronic level detector 17 and a level adjusting valve 19 are provided. The regenerated liquid from the flash vessel was then recycled - free of methanol - to the absorber with the high pressure pump 21. The expansion valves 18 were adjusted automatically to maintain a constant liquid level in the flash vessels. The flash vapours were led through a cold trap 11 where methanol condensed.

Gas samples could be taken at sampling points 5 at the inlet and the outlet of every reactor. The gas analyses were carried out with a Varian series 3700 chromatograph with a thermal conductivity detector and a Porapak Q column of 2.5 m long and $\frac{1}{4}'$ in diameter. Automatic on-line gas analysis was possible.

The liquid could be sampled at sampling points 14 at the inlet and the outlet of the absorption column and also in the outlet of the first flash vessel if the two-stage system for desorption was in use. The methanol content of the solvent was determined by refractometric analysis.

All the elements of the miniplant were made of 316 stainless steel. The composition of the reactant gases used is specified in Table 1.

EXAMPLES

Example 1 (one-stage expansion)

Figure 3:
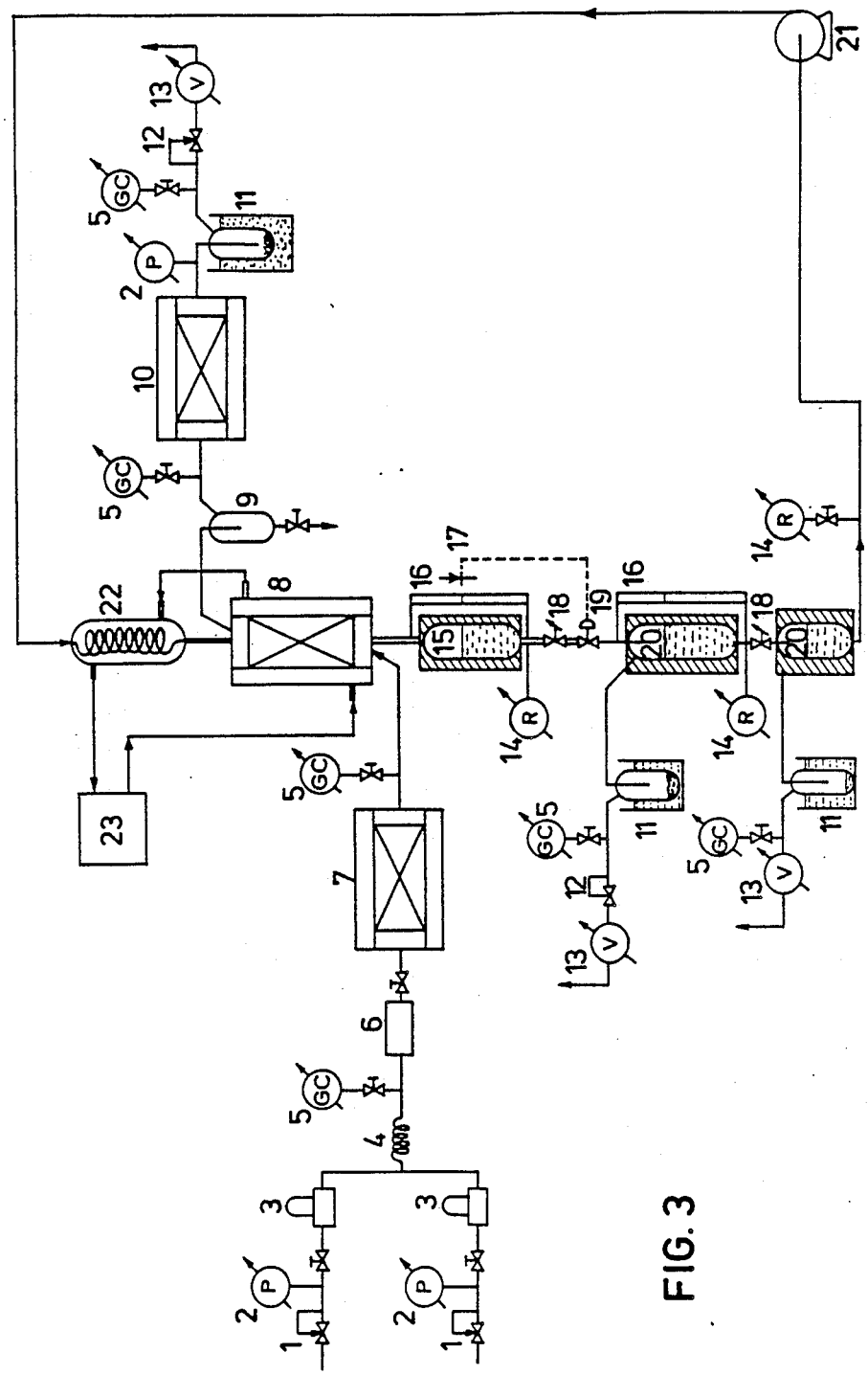

The high pressure miniplant of FIG. 3 was operated under the following steady-state conditions:

| Total pressure | 8.1 MPa abs. |
| --- | --- |
| Feed gas composition | 33 vol % CO, 67 vol % $H_2$ |
| Flow rate of the feed gas | $4.9 * 10^{-3}$ mol/s |
| Temperatures: first reactor | 265° C. |
| second reactor | 250° C. |

The absorber column was maintained at a temperature of 200° C. and there was first no supply of solvent to the absorber. At these conditions, a methanol production rate of $1.12*10^{-3}$ mol/s was measured, so the total degree of conversion of carbon monoxide as achieved in the two reactors was 69%.

Subsequently with the two reactors in operation the absorption was started and the solvent TEGDME was led through the column at a constant flow rate of $0.119*10^{-3}$ kg/s. The first flash vessel was operated at a temperature of 200° C. and under a pressure of 0.2 MPa abs., whereas the second expansion stage was bypassed. After a steady state had been reached again the methanol production rate was again determined. The total methanol production was now $1.37*10^{-3}$ mol/s, corresponding to an over-all CO-conversion of 85%. Of the total methanol production, $0.81*10^{-3}$ mol/s left the reactor in the gaseous effluent of the second reactor and the remaining $0.56*10^{31\ 3}$ mol/s were received from the expansion vessel. The co-absorbed synthesis gas was released in the expansion vessel at a rate of $41.7*10^{-6}$ mol/s, the absorber inlet contained $3.25*10^{-3}$ mol/s synthesis gas.

From the refractometric analysis it was found that the methanol content in the saturated solvent leaving the absorber was 0.15 g/g solvent. The concentration level in the regenerated liquid was so low that a quantitative determination was impossible (far below 0.3 g/g solvent).

The absorber absorbed 68% of the methanol contained in the reactor product of reactor 1. By calculation it was shown that the column contained $3\frac{1}{2}$ theoretical plates. So the HETP was 0.115 m leading to the conclusion that the absorber performed very efficiently. By calculation it also can be shown that the absorber should have had a height of 1.1 m in order to absorb 90% of the methanol in the inlet stream. The absorption factor was equal 0.75.

Example 2 (two stage expansion)

To illustrate the operation of the two-stage desorption system, an experiment has been carried out under conditions identical to those in Example 1, but with both expansion stages in operation. The first flash vessel was operated at 2 MPa pressure and the second one at 0.2 MPa. Both vessels were maintained at the same

TABLE 1

| | Volumetric composition of the feed gases (manufacturers specification). | | | | | | | |
| --- | --- | --- | --- | --- | --- | --- | --- | --- |
| component gas | CO | $H_2$ | $H_2$ | $N_2$ | $CO_2$ | Ar | hydrocarbons | $H_2O$ |
| CO | >99.5% | <0.1% | — | <0.3% | — | <0.3% | <200 ppm | — |
| $H_2$ | <5 ppm | >99.9% | <5 ppm | <5 ppm | <5 ppm | — | — | <300 ppm | temperature of 200° C. Under steady-state conditions, after the first stage, the co-absorbed synthesis gas was released at a rate of $29.7*10^{-6}$ mol/s. After the second stage $12*10^{-6}$ mol/s synthesis gas were released, so the total amount of the synthesis gas recovered by expansion was the same as in Example 1. Also the same methanol desorption rate has been measured being $0.56*10^{-3}$ mol/s; practially the entire amount of methanol was released after the second stage. Only a very small amount of methanol was found in the effluent of the first stage, so that quantitative determination was impossible.

I claim:

1. A process for producing methanol by reacting carbon monoxide and hydrogen and optionally carbon dioxide reactants, comprising introducing said reactants in the gaseous phase into a reaction zone of a fixed catalyst bed, feeding the effluent from the reaction zone without cooling it to an adsorption zone where methanol is absorbed using an absorbent which selectively absorbs substantially all of the methanol formed and which is a liquid under reaction circumstances and feeding the mixture obtained to a desorption zone where the methanol is desorbed.

2. A process according to claim 1, characterized in that the absorption zone and the reaction zone are operated at about the same temperature.

3. A process according to claim 1 or 3, characterized in that the unreacted reactants after the absorption step are fed to one or more subsequent reaction zones and adsorption zones as defined in the preceding claims.

4. A process according to claim 4, characterized in that the unreacted reactants are recycled to the reaction zone.

5. A process according to claims 4, characterized in that the subsequent reaction zones and absorption zones are smaller than the preceding ones.

6. A process according to claim 5 characterized in that four systems comprising a reaction zone and an absorption zone are used.

7. A process according to claim 6, characterized in that methanol is desorbed from the liquid absorbent by flashing to a lower pressure.

8. A process according to claim 7, characterized in that the pressure is decreased in two steps, wherein in the first stage predominantly absorbed synthesis gas is released which is recycled to one of the reaction zones, and in the second stage predominantly methanol is released.

9. A process according to claim 8 characterized in that the liquid absorbent is tetraethylene glycol dimethyl ether.

* * * * *